(12) United States Patent
Albrecht et al.

(10) Patent No.: US 6,613,535 B1
(45) Date of Patent: Sep. 2, 2003

(54) HLA-B27 ASSAY

(75) Inventors: Joachim Albrecht, Heidelberg (DE); Frank Hulstaert, Zwijnaarde (BE); Rosette Becker, Palo Alto, CA (US)

(73) Assignee: Becton, Dickinson andCompany, Franklin Lakes, NJ (US)

( * ) Notice: Subject to any disclaimer, the term of this patent is extended or adjusted under 35 U.S.C. 154(b) by 0 days.

(21) Appl. No.: 07/968,553

(22) Filed: Oct. 29, 1992

(51) Int. Cl.⁷ .............................................. G01N 33/53

(52) U.S. Cl. ..................... 435/7.24; 435/7.1; 435/967; 435/968; 436/518; 436/529; 436/536; 436/546; 436/8; 436/16; 436/10; 436/172; 436/805; 436/811; 530/388.7; 530/388.75; 530/391.3

(58) Field of Search ................................ 435/7.24, 967, 435/968; 436/518, 529, 536, 546, 8, 16, 10, 172, 805, 811; 530/388.7, 388.75, 391.3

(56) References Cited

U.S. PATENT DOCUMENTS

| | | | | |
|---|---|---|---|---|
| 4,447,528 A | * | 5/1984 | Ellis et al. | 435/7.1 |
| 5,059,524 A | * | 10/1991 | McKenzie et al. | 435/7.24 |
| 5,073,497 A | * | 12/1991 | Schwartz | 436/8 |
| 5,369,010 A | * | 11/1994 | Nelson et al. | |

OTHER PUBLICATIONS

DAKO Bulletin, "The CD System", 1989, DAKO Corporation, USA.*

* cited by examiner

Primary Examiner—Bao-Thuy L. Nguyen

(57) ABSTRACT

This invention relates to a method for establishing and using a decision marker by which positive samples can be discriminated from negative samples. The method employs the analysis of multiple samples from confirmed positive and negative samples. A fluorescence channel is selected so that the desired sensitivity and specificity are achieved. A microparticle having this fluorescence channel then is made and is used in conjunction with a fluorescence marker which is specific for the population of interest.

8 Claims, 2 Drawing Sheets

HLA-B27 ASSAY

FIELD OF THE INVENTION

This invention relates to a method for establishing and using a decision point in flow cytometry wherein the decision point defines a point on the axis of a fluorescence histogram for a fluorescent marker of interest such that if the median channel number of cells stained with that fluorescent marker is greater than the decision point then the sample is said to be "positive" for the fluorescence marker used. The invention more particularly relates to a method for using a fluorescent microparticle as a a control to adjust/monitor the decision point in a flow cytometer. The microparticle having a specified fluorescence which corresponds to the point on the fluorescence histogram when used in conjunction with a fluorescently labelled anti-HLA-B27 monoclonal antibody. When a patient sample is tagged with a fluorescently labelled anti-HLA-B27 antibody, if the median fluorescence channel exceeds the decision point, the patient is said to be "HLA-B27$^+$."

BACKGROUND OF THE INVENTION

Flow cytometry comprises a well known methodology for identifying and distinguishing between different cell types in a non-homogeneous sample. The sample may be drawn from a variety of sources such as blood, lymph, urine, or may be derived from suspensions of cells from solid tissues such as spleen, lymph node or liver. In the flow cytometer, cells are passed substantially one at a time through one or more sensing regions wherein each cell is illuminated by an energy source. The energy source generally comprises means that emits light of a single wavelength in a sensing region such as that provided by a laser (e.g., He/Ne or argon) or a mercury arc lamp with appropriate bandpass filters. Different sensing regions can include energy sources that emit light at different wavelengths.

In series with each sensing region, various light collection means, such as photomultiplier tubes, are used to gather light that is refracted by each cell (generally referred to as forward light scatter), light that is reflected orthogonal to the direction of the flow of the cells through a sensing region (generally referred to as orthogonal or side light scatter) and one or more light collection means to collect fluorescent light that may be emitted from the cell, if it has been tagged with one or more fluorescent markers, as it passes through a sensing region and is illuminated by the energy source. Light scatter is generally correlated with physical characteristics of each cell such as size and granularity.

Flow cytometers further comprise data recording and storage means, such as a computer, wherein separate channels record and store the light scattered and fluorescence emitted by each cell as it passes through a sensing region (i.e., the data collected for each cell comprises a "recorded event"). The recorded events then can be displayed by plotting orthogonal light scatter versus forward light scatter in either real time or by reanalysis of the data after the events have been recorded. U.S. Pat. Nos. 4,599,307 and 4,727,020 describe of the various components that comprise a flow cytometer and also the general principles of its use.

Monoclonal antibodies are particularly useful in flow cytometry when conjugated, directly or indirectly, to fluorescent dyes (generically this combination is referred to as an "immunofluorescent marker"). Monoclonal antibodies have been made against a large number of antigens present on and within cells. Such antibodies are used to identify certain populations of hematopoietic cells as well as subpopulations thereof. An immunofluorescent marker is added to a sample of cells and the sample then is analyzed by means of flow cytometry. The light emitted by the fluorescent dye as it is excited by the energy source is stored and recorded as described above. PCT Appl. No. PCT/CA92/00105 describes the extent to which monoclonal antibodies have been and are being used to identify various cell populations and subpopulations.

When a recorded event includes fluorescent data, the data can be displayed in a fluorescence histogram such as is shown in FIG. 2 of U.S. Pat. No. 4,727,020. If multiple immunofluorescent markers are used (wherein each dye has an emission spectra that is distinguishable from the other dyes used), the data for a recorded event can be displayed in a multi-dimensional format such as shown in FIG. 3 of the same patent.

Looking more closely at FIG. 2a in that patent, it can be seen that not all cells express the same amount of fluorescence. This may be due to reaction conditions or may be due to differences between the levels of expression of the antigen on the cell. It also can be seen that there are a large number of cells that have little or no fluorescence intensity. Generally, these cells would be referred to as being "negative" for expression of the immunofluorescent marker while the remaining cells would be referred to as being "positive" for the immunofluorescent marker.

Looking at FIG. 3, one can distinguish between cells on the x and y axes that are clearly "positive" (i.e., they are far away from the origin), and cells in the bottom left corner of the figure that are "negative" (i.e., they are close to the origin). For both FIG. 2 and FIG. 3, however, it is not immediately apparent from the displays which cells should be characterized definitively as belonging in either class nor is it apparent that one would classify the individual from whom this sample was taken as being positive or negative for the markers used.

Because the level of fluorescence intensity for any given population of tagged cells in a sample is not always clear, many methods have been developed to try to separate "positive" and "negative" cells. U.S. Pat. No. 4,987,086 describes a gating method which can be used to set boundaries or "gates" in a two dimensional display in order to distinguish between such cells. The method makes use of scatter parameters and fluorescent parameters to arrive at a decision point for each fluorescent marker as to the boundary between positive and negative cells.

The information provided by the method described in U.S. Pat. No. 4,987,086, however, relates only to a calculation of the number of cells present in one or more cell populations or subpopulations for the individual sample being examined. It does not give an indication whether a particular sample can be said to be "positive" or "negative" for the a particular marker when that marker is viewed in the context of a population of patients. For example, in certain diseases, the presence or absence of a particular marker may be indicative of a disease state or of susceptibility to such disease. In a sample taken from a patient, there may be individual cells that are "positive" or "negative" on a fluorescence plot of those cells. The plot will have a median fluorescence channel. Unless the channel number for that patient's sample is compared with a decision point derived from a population of patients, the total number of cells which are positive or negative does not make full use of the information present. Thus, merely classifying each cell as positive or negative for a marker is not enough.

SUMMARY OF THE INVENTION

The present invention comprises a method to identify and set a decision point in order to discriminate between a positive and negative sample of cells wherein those cells have been tagged with a fluorescent marker. The decision point comprises a decision point on a fluorescence axis. The decision point is set so that it corresponds to the fluorescence channel at the desired sensitivity and specificity for the fluorescent marker. This is done by analysis of known patient samples. In a preferred embodiment, the desired sensitivity is 100% and the desired specificity is at least 97%. If a patient sample that has been tagged with a fluorescent marker which is specific for the cell marker of interest has a median channel number greater than the decision point, the sample is said to be "positive" for that marker.

The decision point may be set in software used in conjunction with the flow cytometer, wherein the software calculates the median channel number for all the recorded events and compares that to the decision point for that marker. Alternatively, or in addition, a microparticle having fluorescence characteristics similar to the fluorescent marker can be used. In this embodiment, the particle is used to adjust/monitor the instrument so that if the decision point were set at "166", the particles can be run on the instrument prior to or at the same time as the fluorescent marker to be sure that the instrument reads 166 as 166.

After the decision point is set, one or more fluorescent markers are added to a sample containing cells. The cells then are run through a flow cytometer as described above. The median fluorescence channel then is determined for the cells tagged with each fluorescence marker. If the median channel number exceeds the decision point for that marker, the population of cells is considered "positive" for expression of that marker.

It should be apparent that multiple fluorescent markers can be used in order to identify or limit the population or subpopulation of cells being analyzed. In this embodiment, it is possible to use combinations of immunofluorescent markers alone in order to identify and isolate certain subpopulations of cells and/or in combination with one or more nucleic acid stains for the same purpose. It further is to be appreciated that multiple decision points can be used in multi-dimensional analysis of data wherein a separate decision point is used in conjunction with each fluorescent marker.

This invention has particular utility in the analysis of blood cells from patients suspected of having certain diseases such as ankylosing spondylitis ("AS"). It is known that certain individuals who are characterized as being HLA-B27$^+$ are more likely to develop such diseases. Thus, typing the individual for HLA type is an important diagnostic tool.

In this embodiment, a fluorescently labelled anti-CD3 monoclonal antibody and a fluorescently labelled anti-HLA-B27 monoclonal antibody are prepared. The fluorescence:protein ratio for the HLA-B27 antibody is determined. It is important that this ratio not vary significantly because the fluorescence intensity of the antibody will effect the median channel number (i.e., if there are fewer fluors on an antibody, then the median channel number of the cells tagged with those antibodies will be lower and therefore could give a potentially false result). A microparticle having similar fluorescence properties as the labelled HLA-B27 antibody also is prepared.

The microparticle is run on the instrument in order to assure that the instrument will read the desired decision point in the proper fluorescence channel. The labelled antibodies then are added to blood. The fluorescently labelled anti-CD3 monoclonal antibody is used in conjunction with forward scatter to gate on only those cells that are positive for this antibody. The median fluorescence channel of the HLA-B27$^+$ T cells falling within the gates then is determined. If the median channel number exceeds the decision marker channel number, the sample is said to be "positive."

DETAILED DESCRIPTION

The current method for HLA-B27 typing is a microlymphocytotoxicity test as described by Terasaki. This method is microscopy based and requires density-gradient separation of lymphocytes and the use of polyclonal antisera. The test often has less than 100% sensitivity or specificity. It is time consuming and requires a trained technician to read the wells of the plate.

U.S. Pat. No. 5,059,524 and PCT/CA92/00105 also describe methods for HLA-B27 typing. The former describes and immunoassay approach to HLA-B27 typing (as well as monoclonal antibodies useful in such assays) while the latter describes various monoclonal antibodies for HLA typing.

In accordance with the present invention, a fluorescently labelled anti-T cell monoclonal antibody and a fluorescently labelled anti-HLA-B27 monoclonal antibody are added to whole blood. The mixture is incubated. The red blood cells then are lysed, washed and fixed prior to being run on a flow cytometer. It is preferred that the anti-T cell antibody be an anti-CD3 monoclonal antibody, such as Leu 4 (Becton Dickinson Immunocytometry System "BDIS"). Leu 4 was derived from hybridization of mouse NS-1 myeloma cells with spleen cells from BALB/c mice immunized with human thymocytes. Anti-HLA-B27 ("BDIS") was derived from the fusion of mouse NS-1 myeloma cells with spleen cells from CB$_6$F$_1$ mice immunized with cells from a HLA-B27 positive B-lymphoblastoid cell line (AS-3). It is preferred that the CD3 antibody be labelled with phycoerythrin ("PE") and the HLA-B27 antibody be labelled with fluorescein isothiocyanate ("FITC"). Other dyes useful in the practice of this invention are described in U.S. Pat. No. 4,745,285, 4,876,190, 4,520,110 and 4,542,104.

Figure 1:
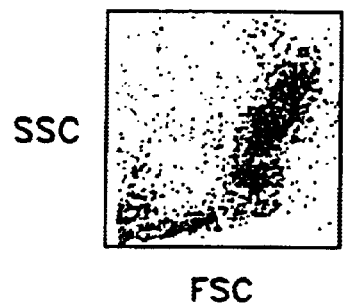
FIG. 1 is a dot plot of forward scatter versus side scatter for blood from a patient whose cells, which were positive for HLA-B27 as confirmed by a Terasaki test, have been tagged with an anti-CD3 PE monoclonal antibody and an anti-HLA-B27 FITC monoclonal antibody.

Forward scatter, side scatter, PE and FITC fluorescence are recorded in the flow cytometer for each cell. It is preferred that 15,000 events be recorded for each sample. A dot plot of forward versus side scatter is shown in FIG. 1 for a sample of blood treated with anti-CD3 PE and anti-HLA-B27 FITC from a confirmed HLA-B27$^+$ patient.

Figure 2:
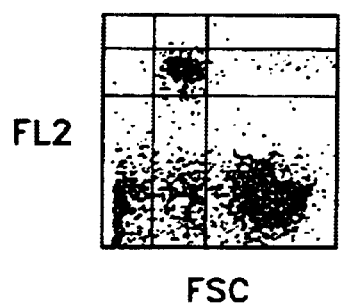
FIG. 2 is a dot plot of log PE fluorescence versus forward scatter for the blood from FIG. 1.
Figure 3:
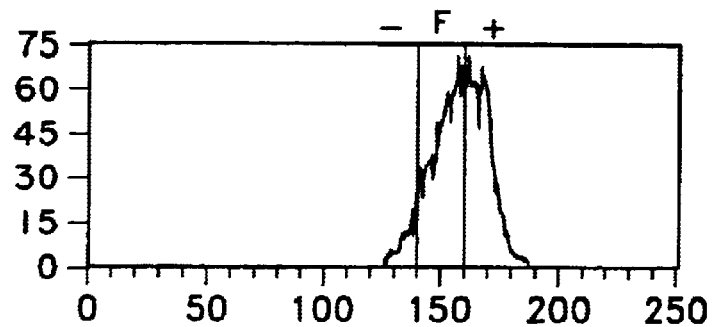
FIG. 3 is a histogram of log FITC fluorescence for those HLA-B27$^+$ cells that fall within the CD3$^+$ gate set in FIG. 2.

Referring to FIG. 2, a plot of forward scatter versus log PE fluorescence was made. In the upper portion of the plot, slightly to the left of center, a distinct population of cells is seen. These cells are CD3+ T cells. Gates then were set in forward scatter and FL2 such that at least 50% of all CD3+ T cells fell within the gates. A histogram of FITC fluorescence then was made, see FIG. 3, and the median fluorescence channel was calculated. The result was compared with the fluorescence channel of the decision marker to determine if the sample of cells is HLA-B27+. If the median is greater than this value, the sample can be considered "positive." In this case, it was. See FIG. 3.

Figure 4:
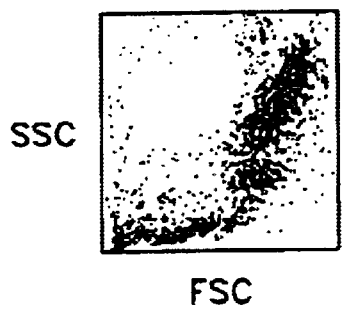
FIG. 4 is a dot plot as in FIG. 1, however, the blood is taken from a patient whose cells were negative as determined by a Terasaki test.
Figure 5:
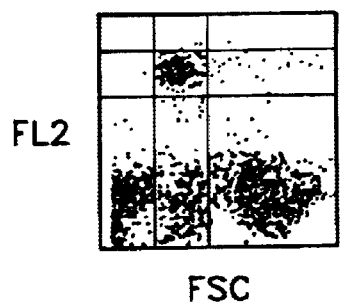
FIG. 5 is a dot plot as in FIG. 2 from the blood of the negative patient.
Figure 6:
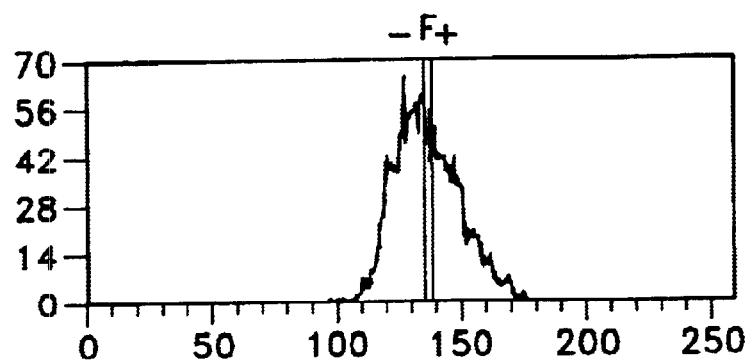
FIG. 6 is a histogram as in FIG. 3 from the blood of the negative patient.

These results should be compared with blood from a patient known to be negative for HLA-B27 as shown in FIGS. 4–6.

In order to establish the parameters for this method and to establish the fluorescence channel for the decision marker, blood samples were examined at two sites using a FACScan brand flow cytometer (BDIS) and associated computer software and hardware using the procedure set forth above. The mean fluorescence channel for each sample was recorded. Table I sets forth the patient sample number and median fluorescence channel at each test site. "Positive" and "negative" samples were confirmed by standard Terasaki procedures.

In Table I, over 310 samples were collected and analyzed. Of the 260 which could be evaluated, there were 47 true positives, 0 false negatives and 4 false positives when the decision marker was set between channel numbers 138–143. This gave a sensitivity of 100% and a specificity of greater than 98%.

Since the time that the data set forth in Table I was collected, additional data has been collected at each site and added to it such that a total of 298 samples were evaluable at one site and 315 samples at the other. Reanalysis of the data provided similar sensitivity and specificity at channel numbers between 132–139. The preferred channel number for the decision point that meets these criteria, therefore, is 136. If one accepts lower sensitivity and specificity, an acceptable range is between 121–146.

TABLE 1

| Study-ID | Pat.-No. | Median | B1 | B2 |
|---|---|---|---|---|
| (SITE 1) | | | | |
| | 170 | | | |
| B27 | 136 | 71 | | |
| B27 | 153 | 73 | | |
| B27 | 140 | 74 | | |
| B27 | 32 | 75 | | |
| B27 | 149 | 75 | | |
| B27 | 144 | 76 | | |
| B27 | 12 | 77 | | |
| B27 | 90 | 77 | | |
| B27 | 100 | 77 | | |
| B27 | 116 | 77 | | |
| B27 | 48 | 78 | | |
| B27 | 107 | 78 | | |
| B27 | 109 | 78 | | |
| B27 | 148 | 78 | | |
| B27 | 106 | 79 | | |
| B27 | 112 | 79 | | |
| B27 | 131 | 79 | | |
| B27 | 8 | 80 | | |
| B27 | 49 | 80 | | |
| B27 | 50 | 80 | | |
| B27 | 95 | 80 | | |
| B27 | 145 | 80 | | |
| B27 | 162 | 80 | | |

TABLE 1-continued

| Study-ID | Pat.-No. | Median | B1 | B2 |
|---|---|---|---|---|
| B27 | 171 | 80 | | |
| B27 | 6 | 81 | | |
| B27 | 7 | 81 | | |
| B27 | 23 | 81 | | |
| B27 | 31 | 81 | | |
| B27 | 88 | 82 | | |
| B27 | 119 | 82 | | |
| B27 | 135 | 82 | | |
| B27 | 150 | 82 | | |
| B27 | 1 | 83 | | |
| B27 | 16 | 83 | | |
| B27 | 40 | 83 | | |
| B27 | 84 | 83 | | |
| B27 | 117 | 83 | | |
| B27 | 122 | 83 | 51 | |
| B27 | 146 | 83 | | |
| B27 | 53 | 84 | | |
| B27 | 93 | 84 | | |
| B27 | 11 | 85 | | |
| B27 | 15 | 85 | | |
| B27 | 39 | 85 | | |
| B27 | 111 | 85 | | |
| B27 | 3 | 86 | | |
| B27 | 5 | 86 | | |
| B27 | 66 | 86 | 51 | |
| B27 | 62 | 87 | | |
| B27 | 67 | 87 | | |
| B27 | 69 | 87 | | |
| B27 | 71 | 88 | | |
| B27 | 133 | 88 | | |
| B27 | 138 | 88 | 51 | |
| B27 | 21 | 90 | 51 | |
| B27 | 86 | 90 | | |
| B27 | 103 | 90 | | |
| B27 | 167 | 90 | 51 | |
| B27 | 79 | 91 | | |
| B27 | 96 | 91 | | |
| B27 | 155 | 91 | | |
| B27 | 41 | 92 | | |
| B27 | 42 | 92 | 51 | |
| B27 | 85 | 92 | | |
| B27 | 102 | 92 | 51 | |
| B27 | 105 | 92 | | |
| B27 | 141 | 92 | 52 | |
| B27 | 30 | 93 | 51 | |
| B27 | 47 | 95 | 51 | |
| B27 | 118 | 95 | | |
| B27 | 123 | 95 | 52 | |
| B27 | 165 | 95 | 51 | |
| B27 | 45 | 96 | 51 | |
| B27 | 158 | 96 | 51 | |
| B27 | 113 | 97 | | |
| B27 | 115 | 97 | | |
| B27 | 161 | 97 | 51 | |
| B27 | 51 | 98 | 51 | |
| B27 | 154 | 98 | | |
| B27 | 168 | 98 | | |
| B27 | 19 | 99 | | |
| B27 | 108 | 99 | | |
| B27 | 10 | 100 | 99 | |
| B27 | 59 | 101 | | |
| B27 | 2 | 102 | | |
| B27 | 63 | 102 | | |
| B27 | 68 | 102 | 51 | |
| B27 | 18 | 103 | 51 | |
| B27 | 38 | 103 | 52 | |
| B27 | 83 | 103 | | |
| B27 | 101 | 103 | 51 | |
| B27 | 97 | 106 | | |
| B27 | 160 | 106 | 52 | |
| B27 | 166 | 106 | | |
| B27 | 13 | 108 | 99 | |
| B27 | 73 | 108 | | |
| B27 | 156 | 108 | 7 | |
| B27 | 132 | 110 | 7 | |
| B27 | 134 | 110 | 7 | |
| B27 | 58 | 112 | | |

TABLE 1-continued

| Study-ID | Pat.-No. | Median | B1 | B2 |
|---|---|---|---|---|
| B27 | 76 | 112 | | |
| B27 | 77 | 114 | 7 | |
| B27 | 82 | 114 | | |
| B27 | 130 | 114 | 7 | |
| B27 | 37 | 115 | 7 | |
| B27 | 55 | 116 | | |
| B27 | 81 | 116 | | |
| B27 | 127 | 116 | 7 | |
| B27 | 44 | 117 | 7 | |
| B27 | 104 | 117 | 51 | |
| B27 | 147 | 117 | 7 | |
| B27 | 34 | 118 | 7 | |
| B27 | 126 | 119 | 99 | |
| B27 | 142 | 119 | 7 | |
| B27 | 157 | 119 | 7 | |
| B27 | 56 | 120 | | |
| B27 | 151 | 120 | 7 | 52 |
| B27 | 129 | 121 | | |
| B27 | 35 | 122 | | |
| B27 | 57 | 122 | 51 | |
| B27 | 28 | 123 | 99 | |
| B27 | 80 | 123 | | |
| B27 | 94 | 123 | 7 | |
| B27 | 139 | 126 | | |
| B27 | 89 | 127 | 7 | 51 |
| B27 | 33 | 128 | 7 | |
| B27 | 17 | 129 | 7 | |
| B27 | 114 | 129 | 7 | 52 |
| B27 | 169 | 130 | 7 | |
| B27 | 26 | 132 | | |
| B27 | 152 | 132 | 7 | |
| B27 | 27 | 133 | 52 | |
| B27 | 124 | 133 | | |
| B27 | 9 | 134 | | |
| B27 | 110 | 136 | 7 | |
| B27 | 121 | 137 | | |
| B27 | 72 | 138 | | |
| B27 | 87 | 138 | | |
| B27 | 92 | 138 | 7 | |
| B27 | 46 | 143 | 7 | |
| B27 | 137 | 143 | 27 | 7 |
| B27 | 159 | 144 | 27 | 7 |
| B27 | 4 | 145 | 7 | |
| B27 | 60 | 145 | 27 | |
| B27 | 170 | 146 | 27 | 7 |
| B27 | 125 | 148 | 27 | 52 |
| B27 | 24 | 151 | 7 | |
| B27 | 29 | 154 | 27 | |
| B27 | 43 | 154 | 27 | |
| B27 | 52 | 154 | 27 | |
| B27 | 65 | 154 | 27 | |
| B27 | 70 | 154 | 27 | |
| B27 | 25 | 157 | 27 | |
| B27 | 128 | 157 | 27 | 7 |
| B27 | 98 | 159 | 27 | |
| B27 | 54 | 160 | 27 | |
| B27 | 61 | 160 | 27 | 51 |
| B27 | 64 | 160 | 27 | |
| B27 | 91 | 160 | 27 | |
| B27 | 22 | 162 | 27 | |
| B27 | 75 | 162 | 27 | |
| B27 | 99 | 163 | 27 | |
| B27 | 163 | 163 | 27 | 7 |
| B27 | 14 | 166 | 27 | |
| B27 | 74 | 16 | 27 | |
| B27 | 164 | 166 | 27 | 7 |
| B27 | 20 | 167 | 27 | 7 |
| B27 | 120 | 170 | 27 | |
| B27 | 78 | 176 | 27 | 7 |
| B27 | 36 | 189 | 27 | |
| | | (SITE 2) | | |
| | | 142 | | |
| B28 | 102 | 74 | 35 | 41 |
| B28 | 130 | 76 | | |
| B28 | 73 | 77 | 44 | 35 |
| B28 | 19 | 78 | 35 | 62 |
| B28 | 67 | 78 | 62 | 35 |
| B28 | 122 | 78 | | |
| B28 | 6 | 79 | 35 | 44 |
| B28 | 74 | 79 | 8 | 35 |
| B28 | 106 | 79 | 18 | 35 |
| B28 | 56 | 80 | 44 | 53 |
| B28 | 110 | 80 | 8 | 44 |
| B28 | 113. | 80 | 8 | 18 |
| B28 | 119 | 80 | | |
| B28 | 124 | 80 | | |
| B28 | 50 | 81 | 45 | 53 |
| B28 | 53 | 81 | 35 | |
| B28 | 62 | 81 | 8 | 41 |
| B28 | 139 | 81 | | |
| B28 | 1 | 82 | 35 | |
| B28 | 30 | 82 | 13 | 44 |
| B28 | 70 | 82 | 13 | 35 |
| B28 | 86 | 82 | 8 | 60 |
| B28 | 88 | 82 | 8 | 14 |
| B28 | 96 | 82 | 35 | 47 |
| B28 | 99 | 82 | 44 | 63 |
| B28 | 111 | 82 | 44 | 17 |
| B28 | 7 | 83 | 22 | 41 |
| B28 | 11 | 83 | 8 | 35 |
| B28 | 71 | 83 | 14 | 18 |
| B28 | 117 | 83 | | |
| B28 | 136 | 83 | | |
| B28 | 60 | 84 | 17 | 35 |
| B28 | 82 | 84 | 8 | 44 |
| B28 | 91 | 84 | 44 | |
| B28 | 61 | 85 | 44 | 60 |
| B28 | 81 | 85 | 22 | 60 |
| B28 | 68 | 86 | 44 | 17 |
| B28 | 90 | 86 | 44 | |
| B28 | 8 | 87 | 8 | 17 |
| B28 | 22 | 87 | 13 | 44 |
| B28 | 32 | 87 | 44 | 60 |
| B28 | 69 | 87 | 44 | 35 |
| B28 | 83 | 87 | 44 | 17 |
| B28 | 84 | 87 | 14 | 39 |
| B28 | 85 | 87 | 51 | 14 |
| B28 | 93 | 87 | 44 | 38 |
| B28 | 78 | 88 | 14 | 18 |
| B28 | 104 | 88 | 44 | 49 |
| B28 | 112 | 88 | 44 | 41 |
| B28 | 116 | 88 | | |
| B28 | 135 | 88 | | |
| B28 | 10 | 89 | 18 | 44 |
| B28 | 15 | 89 | 17 | 62 |
| B28 | 25 | 89 | 18 | 35 |
| B28 | 38 | 89 | 8 | 38 |
| B28 | 55 | 89 | 44 | 45 |
| B28 | 66 | 89 | 51 | 35 |
| B28 | 125 | 89 | | |
| B28 | 128 | 89 | | |
| B28 | 23 | 90 | 18 | |
| B28 | 123 | 90 | | |
| B28 | 20 | 91 | 35 | 38 |
| B28 | 27 | 91 | 12 | |
| B28 | 9 | 92 | 51 | 8 |
| B28 | 17 | 93 | | 18 |
| B28 | 54 | 93 | 51 | 35 |
| B28 | 98 | 93 | 44 | 49 |
| B28 | 79 | 95 | 8 | 63 |
| B28 | 97 | 95 | 51 | 44 |
| B28 | 126 | 95 | | |
| B28 | 13 | 96 | 14 | 41 |
| B28 | 29 | 97 | 51 | 17 |
| B28 | 57 | 97 | 51 | 62 |
| B28 | 24 | 98 | 51 | 8 |
| B28 | 2 | 99 | 62 | 60 |
| B28 | 137 | 100 | | |
| B28 | 44 | 101 | | |
| B28 | 21 | 102 | 51 | 35 |
| B28 | 63 | 103 | 51 | 18 |
| B28 | 118 | 103 | | |
| B28 | 42 | 104 | 38 | 62 |

TABLE 1-continued

| Study-ID | Pat.-No. | Median | B1 | B2 |
|---|---|---|---|---|
| B28 | 52 | 105 | 51 | |
| B28 | 105 | 106 | | 49 61 |
| B28 | 131 | 107 | | |
| B28 | 51 | 109 | | |
| B28 | 40 | 110 | 51 | 5 62 |
| B28 | 141 | 110 | | |
| B28 | 100 | 111 | 7 | 44 |
| B28 | 103 | 111 | 52 | 61 |
| B28 | 129 | 111 | | |
| B28 | 142 | 112 | | |
| B28 | 76 | 113 | | 39 35 |
| B28 | 37 | 114 | | 39 44 |
| B28 | 49 | 116 | 7 | 62 |
| B28 | 108 | 116 | 7 | 44 |
| B28 | 16 | 117 | 7 | 44 |
| B28 | 92 | 117 | 7 | 62 |
| B28 | 120 | 117 | | |
| B28 | 3 | 118 | 7 | 62 |
| B28 | 46 | 118 | | 44 39 |
| B28 | 115 | 118 | | |
| B28 | 80 | 120 | 7 | 35 |
| B28 | 109 | 120 | 7 | 51 |
| B28 | 4 | 121 | 7 | 8 |
| B28 | 127 | 122 | | |
| B28 | 134 | 122 | | |
| B28 | 39 | 123 | 52 | 18 |
| B28 | 72 | 123 | | 17 37 |
| B28 | 89 | 123 | | 62 37 |
| B28 | 12 | 124 | 7 | 44 |
| B28 | 36 | 124 | 7 | 65 |
| B28 | 34 | 125 | 7 | 51 |
| B28 | 59 | 126 | | 8 14 |
| B28 | 132 | 126 | | |
| B28 | 31 | 127 | 52 | 51 |
| B28 | 114 | 127 | | |
| B28 | 94 | 128 | 7 | 22 |
| B28 | 18 | 133 | 7 | 39 |
| B28 | 5 | 139 | 7 | 39 |
| B28 | 35 | 139 | 7 | |
| B28 | 45 | 145 | 7 | 39 |
| B28 | 33 | 155 | 27 | 17 |
| B28 | 140 | 155 | 27 | |
| B28 | 26 | 157 | 27 | 35 |
| B28 | 121 | 157 | 27 | |
| B28 | 43 | 158 | 27 | 18 |
| B28 | 58 | 158 | 27 | 35 |
| B28 | 64 | 159 | 27 | 13 |
| B28 | 28 | 160 | 27 | 44 |
| B28 | 14 | 161 | 27 | 50 |
| B28 | 41 | 161 | 27 | 45 |
| B28 | 47 | 161 | 27 | 62 |
| B28 | 48 | 162 | 27 | 62 |
| B28 | 75 | 163 | 27 | 35 |
| B28 | 138 | 163 | 27 | |
| B28 | 77 | 164 | 27 | 62 |
| B28 | 107 | 164 | 27 | 51 |
| B28 | 65 | 165 | 27 | 7 |
| B28 | 101 | 165 | 27 | 13 |
| B28 | 95 | 166 | 27 | 7 |
| B28 | 133 | 166 | 27 | |
| B28 | 87 | 168 | 27 | 18 |

99 = Cytox. not readable
100 = no gate

Having performed these studies, a microparticle was developed that corresponds to a channel number of about 136. This microparticle comprises a polystyrene bead of about 7.0 μ. It contains a yellow-green fluorescent composition which has fluorescent properties similar to FITC. It is manufactured by Molecular Probes, Inc.

To carry out the method of this invention, therefore, data has been collected on a large number of patient samples in order to establish a fluorescence channel number for HLA-B27 fluorescence as a decision point. A microparticle having a fluorescence channel number substantially equal to that number then was prepared. A suspension containing those microparticles then is analyzed on a flow cytometer and the instrument is calibrated in accordance with the manufacturer's instructions so that the instrument reads the particles at the specified channel number. Each lot of such particles comes with a channel number certified by the manufacturer so that the instrument can be adjusted based upon lot to lot variability.

A sample of blood then is mixed with an immunofluorescent marker. The median channel number of the cells that express that marker is calculated and the result compared with the decision point.

For HLA-B27, two immunofluorescent markers are used: one, anti-CD3 PE is used in conjunction with forward scatter to establish a gate within which the cells will be analyzed; the other, anti-HLA-B27 FITC is the immunofluorescence marker for the population of interest. A 7.0 μ yellow-green fluorescent polystyrene bead with a fluorescence channel number of 136 is used as the decision point in the flow cytometer. Median fluorescence channel number values above this indicate that the sample represents a positive HLA-B27 individual.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed:

1. A method for establishing a decision point in order to determine if an unknown sample of cells is positive or negative for a marker comprising the steps of:
    a) tagging multiple samples of cells which are known to be positive or negative for the presence of the marker with a fluorescent marker that is specific for the marker of interest;
    b) analyzing each of samples of tagged cells by means of flow cytometry and recording the median fluorescence channel for each sample;
    c) setting acceptance criteria for assay sensitivity and specificity;
    d) determining the fluorescence channel number at which the criteria are met and
    e) utilizing said fluorescence channel number as the decision point such that samples having a median fluorescence channel that exceeds the decision point are classed positive for the marker.

2. The method of claim 1 wherein the following step is added:
    preparing a fluorescent microparticle having a fluorescence substantially equal to the channel number selected.

3. A method for the use of decision point in order to determine if an unknown sample of cells is positive or negative for a marker of interest comprising the steps of:
    a) tagging an unknown sample containing cells with a fluorescent marker that reacts specifically with the marker of interest;
    b) analyzing the cells by means of flow cytometry;
    c) calculating the median fluorescence channel number for the sample;

d) comparing the median channel number with the decision point from claim 1; and e) classing the samples as positive for said marker if said median fluorescence channel number exceeds said decision point.

4. The method of claim 1 wherein the marker of interest is HLA-B27.

5. The method of claim 3 wherein the marker of interest is HLA-B27 and the fluorescent marker is a fluorescently labelled anti-HLA-B27 monoclonal antibody.

6. The method of claim 5 wherein step a) is modified so as to include additional fluorescent markers.

7. The method of claim 6 wherein an additional fluorescent marker includes a fluorescently labelled anti-T cell monoclonal antibody.

8. The method of claim 7 wherein the anti-T cell monoclonal antibody is an anti-CD3 monoclonal antibody.

* * * * *